US010220079B2

(12) United States Patent
Blumenfeld

(10) Patent No.: US 10,220,079 B2
(45) **Date of Patent: *Mar. 5, 2019**

(54) SUTURE LINE ADMINISTRATION TECHNIQUE USING BOTULINUM TOXINS

(71) Applicant: Allergan, Inc., Irvine, CA (US)

(72) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,573

(22) Filed: Nov. 27, 2017

(65) Prior Publication Data

US 2018/0078622 A1 Mar. 22, 2018

Related U.S. Application Data

(63) Continuation of application No. 15/012,259, filed on Feb. 1, 2016, now Pat. No. 9,827,297, which is a continuation of application No. 14/086,760, filed on Nov. 21, 2013, now Pat. No. 9,248,168, which is a continuation of application No. 12/062,372, filed on Apr. 3, 2008, now Pat. No. 8,617,571.

(51) Int. Cl.
*A61K 38/48* (2006.01)

(52) U.S. Cl.
CPC .. *A61K 38/4893* (2013.01); *C12Y 304/24069* (2013.01)

(58) Field of Classification Search
None
See application file for complete search history.

(56) References Cited

U.S. PATENT DOCUMENTS 5,437,291 A 8/1995 Pasricha et al.
5,670,484 A 9/1997 Binder
5,714,468 A 2/1998 Binder .............. A61K 38/4893 424/780
5,766,605 A 6/1998 Sanders et al.
5,989,545 A 11/1999 Foster et al.
6,063,768 A 5/2000 First
6,139,845 A 10/2000 Donovan
6,299,893 B1 10/2001 Schwartz et al.
6,306,423 B1 10/2001 Donovan et al.
6,312,708 B1 11/2001 Donovan
6,358,917 B1 3/2002 Carruthers et al.
6,423,319 B1 7/2002 Brooks et al.
6,447,787 B1 9/2002 Gassner et al.
6,458,365 B1 10/2002 Aoki et al.
6,464,986 B1 10/2002 Aoki et al.
6,623,742 B2 9/2003 Voet
6,787,517 B1 9/2004 Gil ...................... A61K 38/168 514/1
8,617,571 B2 * 12/2013 Blumenfeld ....... A61K 38/4893 424/184.1
8,617,572 B2 12/2013 Blumenfeld .............. 424/247.1
8,734,810 B2 5/2014 Blumenfeld .............. 424/239.1
9,066,851 B2 * 6/2015 Borodic .................. A61K 8/02
9,238,061 B2 1/2016 Blumenfeld ....... A61K 38/4893
9,248,168 B2 * 2/2016 Blumenfeld ....... A61K 38/4893
9,827,297 B2 * 11/2017 Blumenfeld ....... A61K 38/4893
2003/0224019 A1 12/2003 O'Brien
2004/0009180 A1 1/2004 Donovan
2004/0028706 A1 2/2004 Aoki et al.
2004/0213811 A1 10/2004 Ackerman
2004/0219172 A1 11/2004 Voet
2005/0191320 A1 9/2005 Turkel
2005/0191321 A1 9/2005 Turkel
2006/0104995 A1 5/2006 Turkel
2006/0121057 A1 6/2006 Turkel
2009/0252764 A1 * 10/2009 Blumenfeld ....... A61K 38/4893 424/239.1
2010/0068244 A1 3/2010 Hughes et al. .............. 424/426
2013/0236446 A1 9/2013 Binder ....................... 424/94.67
2013/0261062 A1 10/2013 Blumenfeld ....... A61K 38/4893 514/18.1
2014/0079687 A1 * 3/2014 Blumenfeld ....... A61K 38/4893 424/94.67
2014/0205590 A1 7/2014 Blumenfeld .............. 424/94.67
2015/0231068 A1 8/2015 Binder ................ A61K 9/0085 424/94.63
2016/0151468 A1 * 6/2016 Blumenfeld ....... A61K 38/4893 424/94.67
2016/0263202 A1 9/2016 Blumenfeld ....... A61K 38/4893

(Continued)

FOREIGN PATENT DOCUMENTS

DE 101 50 415 A1 5/2003
WO WO 95/30431 11/1995

(Continued)

OTHER PUBLICATIONS

Wieckiewicz et al, Toxins, 2017, 9:370, 8 pages. published: Nov. 15, 2017 (Year: 2017).*
U.S. Appl. No. 10/731,973, First, Eric R., filed Dec. 9, 2003.
U.S. Appl. No. 10/752,869, First, Eric R., filed Jan. 1, 2004.
Agur, A.M.R. and Dalley II, A.F., (2005) *Atlas of Anatomy*, $11^{th}$ Ed., Lippincott Williams & Wilkins, Philadelphia, pp. 316, 317, 600, 601, 736.
Aoki K., et al, *Mechanisms of the antinociceptive effect of subcutaneous Botox: Inhibition of peripheral and central nociceptive processing*, Cephalalgia Sep. 2003;23(7):649.
Aoki KR. Evidence for antinociceptive activity of botulinum toxin type A in pain management. Headache 2003;43 Suppl 1:S9-15.
Aoki KR. Pharmacology and immunology of botulinum toxin serotypes. J Neurol 2001;248 Suppl 1:1/3-1/10.
Aoki, Current Medicinal Chemistry, 11:3085-3092, 2004.
Aoki, K., et at, *Botulinum toxin type A and other botulinum toxin serotypes: a comparative review of biochemical and pharmacological actions,* Eur J. Neurol 2001: (suppl 5); 21.29.

(Continued)

*Primary Examiner* — Nita M. Minnifield
(74) *Attorney, Agent, or Firm* — Brigitte C. Phan

(57) ABSTRACT

The present invention utilizes patient-specific landmarks in order to treat headache pain. In one aspect, the present invention relates to the administration of Clostridial toxins, such as a botulinum neurotoxin, to a patient suffering from a headache pain, where the location of administration of the botulinum toxin is based upon at least one suture line of the patient's skull.

20 Claims, 6 Drawing Sheets

(56) References Cited

U.S. PATENT DOCUMENTS

| | | | | |
|---|---|---|---|---|
| 2017/0173123 A1 | 6/2017 | Blumenfeld | A61K 38/4693 | |
| 2017/0232080 A1* | 8/2017 | Binder | A61K 38/4893 424/94.67 | |
| 2018/0078622 A1* | 3/2018 | Blumenfeld | A61K 38/4893 | |

FOREIGN PATENT DOCUMENTS

| | | |
|---|---|---|
| WO | WO 03/011333 | 2/2003 |
| WO | WO 2005/082339 A2 | 9/2005 |
| WO | WO 2006/083455 A1 | 8/2006 |

OTHER PUBLICATIONS

Aoki, K., *Physiology and pharmacology of therapeutic botulinum neurotoxins,* in Kreyden, O., editor, Hyperhydrosis and botulinum toxin in dermatology, Basel, Karger; 2002; 30: pp. 107-116, at 109-110.

Bhattacharya K., et al., *Novel uses of botulinum toxin type A: two case reports,* Mov Disord 2000; 15(Suppl 2):51-52.

Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002;22:432-438.

Bigalke H., et al., *Botulinum A Neurotoxin Inhibits Non-Cholinergic Synaptic Transmission in Mouse Spinal Cord Neurons in Culture,* Brain Research 360;318-324:1985.

Bigalke H., et al., *Tetanus Toxin and Botullnum A Toxin Inhibit Release and Uptake of Various Transmitters, as Studied with Particulate Preparations From Rat Brain and Spinal Cord,* Naunyn-Schmiedeberg's Arch Pharmacol 316;244-251:1981.

Binder WJ, Brin MF, Blitzer A. Botulinum toxin type A (BOTOX) for treatment of migraine headaches: an open-label study. Otolaryngol Head Neck Surg 2000:123(6):669-676.

Binz T. et al., *The Complete Sequence of Botulinum Neurotoxin Type A and Comparison with Other Clostridial Neurotoxins,* J Biological Chemistry 265(16);9153-9158:1990.

Blugerman G., et al., *Multiple eccrine hidrocystomas: A new therapeutic option with botulinum toxin,* Dermatol Surg May 2003;29(5):557-9.

Blumenfeld AM, Dodick DW, Silberstein SD. Botulinum neurotoxin for the treatment of migraine and other primary headache disorders. Dermatol Clin 2004;22:167-175.

Blumenfeld AM. Botulinum toxin type A as an effective prophylactic treatment in primary headache disorders, Headache 2003;43:853-860.

BOTOX® (package insert), Irvine, California: Allergan Inc; 2004.

Brandes JL, Saper JR, Diamond M, et al. Topiramate for migraine prevention: a randomized controlled trial. JAMA;2004;291:965-973.

Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Brin et al., *Report of the Therapeutics and Technology Assessment Subcommittee of the American Academy of Neurology*, Neurology, 40:1332-1336, 1990.

Brin MF, Fahn S, Moskowitz C, et al. Localized injections of botulinum toxin for the treatment of focal dystonia and hemifacial spasm. Movement Dis 1987;2:237-254.

Brin MF, Swope DM, O'Brien C, et al. BOTOX® for migraine: double-blind, placebo-controlled, region-specific evaluation. Cephalalgia 2000;20:421-422.

Brin, M., et at., *Botulinum toxin type A: pharmacology*, In Mayer N., editor, Spasticity: etiology, evaluation, management and the role of botulinum toxin, 2002; pp. 110-124, at 112-113.

Bushara K., *Botulinum toxin and rhinorrhea*, Otolaryngol Head Neck Surg 1996;114(3):507.

Cao, Y., et al. Functional MRI of chronic daily headache. Cephalalgia 1999;19:462-463.

Castillo JP, Munoz P, Guitera V, et al. Epidemiology of chronic daily headache in the general population. Headache 1999;39:190-196.

Cheshire WP, Abashian SW, Mann JD. Botulinum toxin in the treatment of myofascial pain syndrome. Pain 1994;59:65-69.

Colas R, Munoz P, Temprano R, et al. Chronic daily headache with analgesic overuse: epidemiology and impact on quality of life. Neurology 2004;62:1338-1342.

Couch JR. Placebo effect and clinical trials in migraine therapy. Meth Prob Migraine Trials, Neuroepid 1987;6:178-185.

Cui M, Khanijou S, Rubino J, et al. Subcutaneous administration of botulinum toxin A reduces formalin-induced pain. Pain 2004;107:125-133.

Cui, M., et al., *Mechanisms of the antinociceptive effect of subcutaneous BOTOX®: inhibition of peripheral and central nociceptive processing*, Naunyn Schmiedebergs Arch Pharmacol 2002: 365 (supp 2): R17.

Dabrowski et al.; *Botulinum toxin as a novel treatment for self mutilation in Lesch-Nyhan syndrome*, Ann Neurol Sep. 2002;52(3 Supp 1):S157.

DasGupta et al., Biochemie, 71:1193-1200, 1989.

Depakote® ER (package insert). Abbott Laboratories; 2003.

Dowson, A.J., et al., *Managing Chronic Headaches in the Clinic*, Int J. Clin Pract., Dec. 2004, 58, 12, pp. 1142-1151.

Duggan et al.; A surbey of Botulinum neurotoxin substrate expression in cells; *Mov Disord*, 10(3):376:1995.

Durham PL, Cady Ryan, Cady Roger. Regulation of calcitonin gene-related peptide secretion from trigeminal nerve cells by botulinum toxin type A: implications for migraine therapy. Headache 2004;35-42.

European Agency for the Evaluation of Medicinal Products. Note for guidance on clinical investigation of medicinal products for the treatment of migraine. Dec. 2003.

Fedinic et al., Boll. 1st. Sieroter Milan, 64: 35-41, 1985.

Foster L, Clapp L, Erickson M, Jabbari B. Botulinum toxin A and chronic low pack pain. A randomized, double-blind study. Neurol 2001;56:1290-1293.

Freund BJ, Schwartz M. Use of botulinum toxin in chronic whiplash-associated disorder. Clin J Pain 2002;18(6 Suppl):S163-S168.

Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Gawade et al., Brain Res., 334:139-146, 1985.

Gladstone JP., Gawel M. *Newer formulations of the triptans: advances in migraine management*, Drugs, 2003;63(21):2285-305.

Gladstone, J., et al., *Chronic Daily Headache: A Rational Approach to a Challenging Problem,* Seminars in Neurology, 2003, vol. 23, No. 3, pp. 265-275.

Goadsby et al., N. Eng. J. Med., 346:257-270, 2004.

Gonelle-Gispert et al.; snap-25a and -25b isoforms are both expressed in insulin-secreting cells and can function in insulin secretion;*Biochem J* 1;339 (pt 1):159-65:1999.

Guyton A.C. et al., Textbook of Medical Physiology, W.B. Saunders Company 1996, ninth edition; 686-688.

Habermann E., et al., *Tetanus Toxin and Botulinum A and C Neurotoxins Inhibit Noradrenaline Release From Cultured Mouse Brain*, J Neurochem 51(2);522-527:1988.

Habermann E., *Inhibition by Tetanus and Botulinum A Toxin of the release of [$^3$H]Noradrenaline and [$^3$H]GABA From Rat Brain Homogenate,* Experientia 44;224-226: 1988.

Habermann, I-Labeled Neurotoxin from Clostridium Botulinum A: Preparation, Binding to Synaptosomes and Ascent to the Spinal Cord; *Nauyn-Schmiedeberg's Arch. Pharmacol.* 1974; 281, 47-56.

*Harrison's Principles of Internal Medicine* (1998), edited by Anthony Fauci et al., 14$^{th}$ edition, published by McGraw Hill.

Harshman et al., Infect. Immun., 62:421-425, 1994.

Headache Classification Committee of the International Headache Society. Classification and diagnostic criteria for headache disorders, cranial neuralgias and facial pain. Cephalalgia 1988;8 Suppl 7:1-96.

Headache Classification Subcommittee of the International Headache Society. The international classification of headache disorders, 2$^{nd}$ ed. Cephalalgia 2004;24 Suppl 1:1-151.

(56) References Cited

OTHER PUBLICATIONS

Heckmann M., et al., *Botulinum toxin type A injection in the treatment of lichen simplex: An open pilot study*, J Am Acad Dermatol Apr. 2002;46(4):617-9.
Hering R, Gardiner I, Catarci T, Witmarch T, Steiner T, de Belleroche J. Cellullar adaptation in migraineurs with chronic daily headache. Cephalalgia 1993:13:261-6.
Herold et al., Anesthesiology, 77:507-512, 1992.
Holroyd KA, Stensland M, Lipchik GL, et al. Psychosocial correlates and impact of chronic tension-type headaches. Headache 2000; 40:3-16.
International Headache Society committee on Clinical Trials in Migraine. Guidelines for controlled trials of drugs in migraine. First edition. Cephalalgia 1991;11:1-12.
Jacks, L., et al., *Idiopathic toe walking: Treatment with botulinum toxin A injection*, Dev Med Child Neurol 2002;44(Suppl 91):6).
Jahanshahi M., et al., *Psychological functioning before and after treatment of torticollis with botulinum toxin*, J Neurol Neurosurg Psychiatry 1992; 55(3): 229-231.
Jankovic J. et al., *Therapy With Botulinum Toxin*, Marcel Dekker, Inc., (1994), pp. 5, 150.
Jakubowski et al Exploding vs Imploding headache in migraine prophylaxis with Botulinum Toxin A Dec. 5, 2006; 125(3): 286-295.
Jost W., *Ten years' experience with botulinum toxin in anal fissure*, Int J Colorectal Dis Sep. 2002; 17(5):298-302.
Katsambas A., et al., *Cutaneous diseases of the foot: Unapproved treatments,* Clin Dermatol Nov.-Dec. 2002;20(6):689-699.
Klapper JA, Mathew NT, Klapper A et al. Botulinum toxin type A (BTX-A) for the prophylaxis of chronic daily headache. Cephalalgia 2000;20:292-293.
Levy D. et al. "Mast cell degranulation activates a pain pathway underlying migraine headache" Jul. 2007—130(1-2): 166-176.
Li Y, et al., *Sensory and motor denervation influences epidermal thickness in rat foot glabrous skin*, Exp Neurol 1997;147:452-462 (see p. 459).
Linde M, Limmroth V, Dahlöf C, on behalf of the headache Masters Programme. Ethical aspects of placebo in migraine research. Cephalalgia 2003;23:491-495.
Linton-Dahlöf, M Linde, Dahlöf C. Withdrawal therapy improves chronic daily headache associated with long-term misuse of headache medication: a retrospective study. Cephalalgia 2000;20:658-662.
Lipton RB, Bigal ME. Chronic daily headache: Is analgesic overuse a cause of a consquence? Neurology 2003;61:154-155.
Lipton RB, Stewart WF. Migraine headaches: edipemiology and comorbidity. Clin Neuroscience 1998;5:2-9.
Loder, E., et al., *Use of Botulinum Toxins for Chronic Headaches: A Focused Review*, The Clinical Journal of Pain, 2002, 18, pp. S169-S176.
Maizels, M., et al., *The Patient with Daily Headaches*, American Family Physician, Dec. 2004, vol. 70, No. 12, pp. 2299-2306.
Manzoni GC, Granella F, Sandrini G, et al. Classification of chronic daily headache by International Headache Society criteria: limits and new proposals. Cephalalgia 1995;15:37-43.
Marjama-Lyons, J., et al., *Tremor-Predominant Parkinson's Disease*, Drugs & Aging 16(4);273-278:2000.
Mathew N, Kaup A, Kailasam J. Botulinum toxin type A modifies chronic migraine further long-term (3years) experience with up to ten sets of treatments. Headache 2003;43:576.
Mathew NT, Reuveni U, Perez F. Transformed or evolutive migraine Headache 1987;27:102-106.
Mauskop A. Botulinum Toxin in the treatment of chronic daily headaches. Cephalaigia 1999;19:453.
Monzon MJ, Lainez MJA. Quality of life in migraine and chronic daily headache patients. Cephalalgia 1998;18:638-643.
Mov Disord 2002; 17(suppl 5): S292.
Moyer E et al., *Botulinum Toxin Toxin Type B: Experimental and Clinical Experience*, being chapter 6, pp. 71-85 of "Therapy With Botulinum Toxin", edited by Jankovic, J. et al. (1994), Marcel Dekker, Inc.
Murry T., et al., *Spasmodic dysphonia; emotional status and botulinum toxin treatment*, Arch Otolaryngol Mar. 1994; 120(3): 310-316.
Naumann et al; Botulinum toxin type A in the treatment of focal, axillary and palmar hyperhidrosis and other hyperhidrotic conditions; *European J. Neurology* 6 (Supp 4): S111-S115:1999.
O'Brien PC, Fleming TR. A multiple testing procedure for clinical trials. Biometrics 1979;35:549-556.
Ondo WG, Vuong KD, Derman HS. Botulinum toxin A for chronic daily headache: a randomized, placebo-controlled, parallel design study. Cephalalgia 2004;24:60-5.
Payne M., et al, *Botulinum toxin as a novel treatment for self mutilation in Lesch-Nyhan syndrome*, Ann Neurol Sep. 2002;52(3 Supp 1):S157.
Pearce, L.B., *Pharmacologic Characterization of Botulinum Toxin For Basic Science and Medicine*, Toxicon 35(9);1373-1412 at 1393.
Purkiss J, Welch M, Doward S, et al. Capsaicin-stimulated release of substance P from cultured dorsal root ganglion neurons: involvement of two distinct mechanisms. Biochem Pharmacol 2000;59:1403-1406.
Rabasseda et al., Toxicon, 26:329-326, 1988.
Ragona et al.; Management of Parotid Sialocele With Botulinum Toxin; *The Laryngoscope* 109:1344-1346:1999.
Rahimtoola H, Buurma H, Tijssen CC, et al. Migraine prophylactic medication usage patterns in The Netherlands. Cephalalgia 2003;23:293-301.
Relja G, Granato A, Maria Antonello R, Zorzon M. *Headache induced by chronic substance use: analysis of medication overused and minimum dose required to induce headache*, Headache. Feb. 2004;44(2):148-53.
Rogers J., at al., *Injections of botulinum toxin A in foot dystonia*, Neurology Apr. 1993;43(4 Suppl 2).
Sanchez-Prieto, J., et al., *Botulinum Toxin A Blocks Glutamate Exocytosis From Guinea Pig Cerebral Cortical Synaptosomes*, Eur J. Biochem 165;675-681:1987.
Sager JR, Lake AE III, Cantrell DT, et al. Chronic daily headache prophylaxis with tizanidine: a double-blind, placebo-controlled, multicenter outcome study. Headache 2002;42:470-482.
Schantz, E.J., et al, *Properties and use of Botulinum toxin and Other Microbial Neuroitoxins in Medicine,* Microbiol Rev. 56;80-99:1992.
Scher AI, Stewart WF, Liberman J, et al. Prevalence of frequent headache in a population sample. Headache 1998;38;497:506.
Schim, J, et al., *Effect of Preventive Treatment with Botufinurn Toxin Type A on Acute Headache Medication Usage in Migraine Patients*, Current Medical Research Opinions, vol. 20, No. 1, 2004, pp. 49-53.
Schwartz BS, Stewart WF, Lipton RB. Loss of workdays and decreased work effectiveness associated with headache in the workplace. J Occup Environ Med 1997;39:320-327.
Sevim, S., et al., *Botulinum toxin-A therapy for palmar and plantar hyperhidrosis,* Acta Neurol Belg Dec. 2002;102(4):167-70.
Siegel S. Non-parametric statistics for the behavioral sciences. New York: McGraw-Hill Book Company, 1956:96:116-127.
Silberstein SD, Lipton RB, Sliwinski M. Classification of daily and near-daily headaches: field trial of revised IHS criteria. Neurology 1996;47:871-875.
Silberstein SD, Lipton RB, Solomon S, Mathew NT. Classification of daily and near-daily headaches: proposed revisions to the IHS criteria. Headache 1994;34:1-7.
Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, 7th ed. New York, NY: Oxford University Press;2001:247-282.
Silberstein SD, Lipton RB. Chronic daily headache. Curr Opin Neurol 2000;13:277-283.
Silberstein SD, Neto W, Schmitt J, et al. Topiramate in migraine prevention. Arch Neurol 2004;61:490-495.
Silberstein SD, Silberstein MM. New concepts in the pathogenesis of headache. Part II. Pain Man 1990;3:334-342.
Silvestrini M, Bartolini M, Coccia M, et al. Topiramate in the treatment chronic migraine. Cephalalgia 2003;23:820-824.
Simpson et al,. Pharmacol. Rev., 33:155-188, 1981.

(56) References Cited

OTHER PUBLICATIONS

Singh, *Critical Aspects of Bacterial Protein Toxins*, pp. 63-84 (chapter 4) of Natural Toxins II, edited by B.R. Singh et al., Plenum Press, New York (1996).
Sloop RR, Cole BA, Escutin RO. Reconstituted botulinum toxin type A does not lose potency in humans if it is refrozen or refrigerated for 2 weeks before use. Neurology. Jan. 1997;48(1):249-53.
Smuts JA, Baker MK, Smuts HM, et al. Prophylactic treatment of chronic tension-type headache using botulinum toxin type A. Eur J Neurol 1999;6(Suppl 4):S99-S102.
Solomon GD, Sokbieranda FG, Genzen JR. Quality of life assessment among migraine patients treated with Sumatriptan. Headache 1995;35:449-454.
Spira PJ, Beran RG. Gabapentin in the prophylaxis of chronic daily headache: a randomized, placebo-controlled study. Neurology 2003;61:1753-1759.
Stewart WF, Lipton RB, Celentano DD, et al. Prevalence of migraine headaches in the United States. Relation to age, income, race and other sociodemographic factors. JAMA 1992;267:64-69.
Suputtitada, A., *Local botulinum toxin type A injections in the treatment of spastic toes*, Am J Phys Med Rehabil Oct. 2002;81(10):770-5.
Tepper and Dodick, Debate: Analgesic overuse is a cause, not a consquence, of chronic daily headache, *Headache*, 2002; 42:543-554.
Tepper, S., et al., *Botulinum Toxin Type A in the Preventive Treatment of Refractory Headaches—Comparison Between Medication Overusers and Nonmedication Overusers Groups*, Cephalalgia, 2003, 23, p. 715, poster P5N86.
Troost BT. Botulinum toxin type A (Botox)in the treatment of migraine and other headaches. Expert Rev Neurotherap 2004;4:27-31.
Wang SJ, Fuh JL, Lu SR, et al. Chronic daily headache in Chinese elderly: prevalence, risk factors and biannual follow-up. Neurology 2000;54:314-319.
Wang SJ, Fuh JL, Lu SR, et al. Quality of life differs among headache diagnoses: analysis of SF-36 survey in 901 headache patients. Pain 2001;89:285-292.
Weigand et al.; I-Labelled Botulinum A Neurotoxin: Pharmacokinetics in Cats after Intramuscular Injection; *Naunyn-Schmiedeberg's Arch. Pharmacol*. 1976;292, 161-165.
Welch KM, Goadsby PJ. Chronic daily headache: nosology and pathophysiology. Curr Opin Neurol 2002;15:287-95. Review.
Wissel J, Muller J, Dressnandt J, Heinen F, Naumann M, Topka H, Poewe W. Management of spasticity associated pain with botulinum toxin A. J Pain Symptom Manage 2000;20:44-9.
Woolf C. et al., *Neuropathic Pain: Aetiology, Symptoms, Mechanisms, and Management,* Lancet 1999; 353: 1959-64.
Zhang et al. "Sensitization and Activation of Intracranial Meningeal Nocieceptors by Mast-Cell Mediators" Journal of Pharmacol Exp Ther. Aug. 2007. 322(2): pp. 806-812.
U.S. Appl. No. 12/256,655, Turkel, filed Oct. 23, 2008.
Loder, E., et al.: "*Use of Botutinum Toxins for Chronic Headaches: a Focused Review*" Clinical Journal of Pain, New York, NY, US, vol. 18, No. 6, Suppl, Nov. 1, 2002 (Nov. 1, 2002), pp. S169-S176, XP009048989, ISSN: 0749-8047, Abstract, Figure 1.
Retzlaff, E., et al.: "*Cranial Suture Enurons and Head Ache*" Anatomical Record, vol. 184, No. 3, 1976, p. 511, XP002544737, ISSN: 0003-276X.
Silberstein, S., et al.: "*Botulinum Toxn Type A as a Migraine Preventitive Treatment*" Headache, Woodbury, NJ, vol. 40, No. 6, Jun. 1, 2000 (Jun. 1, 2000), pp. 446-450, XP002182692, ISSN: 0017-8748, Abstract: Figure 1.
Blumenfeld et al, Operative Techniques in Otolaryngology—Head and Neck Surgery, vol. 15, No. 2 (JUN), 2004: pp. 90-96.
Dodick et al, Clinics in Dermatology, 2004; 22:76-81.
Schulte-Mattler et al, Pain, 109 (2004) 110-114.
Gupta et al, Headache, Jun. 2011, pp. 1029-1045.
Calandre et al, european J. Neurology, 2006, 14:244-249.
Wilson, Plastic and Reconstructive Surg., May 2006, 117:6:1758-1766.

* cited by examiner

SUTURE LINE ADMINISTRATION TECHNIQUE USING BOTULINUM TOXINS

CROSS REFERENCE

This application is a continuation of U.S. application Ser. No. 15/012,259, filed Feb. 1, 2016, now U.S. Pat. No. 9,827,297, which is a continuation of U.S. application Ser. No. 14/086,760, filed Nov. 21, 2013, now U.S. Pat. No. 9,248,168, which is a continuation of U.S. application Ser. No. 12/062,372, filed Apr. 3, 2008, now U.S. Pat. No. 8,617,571, the contents of which are hereby incorporated by reference in their entirety.

BACKGROUND

The present invention relates to a novel approach to treating a cranial pain, for example, a headache pain, utilizing patient-specific landmarks. In one aspect, the present invention relates to the administration of Clostridial toxins, such as a botulinum neurotoxin, to a patient suffering from a headache pain, where the location of administration of the botulinum toxin is in the vicinity of, and based upon, at least one suture line of the patient's skull.

Pathophysiology of various cranial pain conditions, such as headaches, continues to be explored. A headache is a pain in the head, such as in the scalp, face, forehead or neck, and can be classified as a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying primary disorder that produces the headache as a symptom of that underlying disorder.

Headaches are additionally classified into various headache types, such as tension headache, cervicogenic headache, sinus headache, cluster headache, migraine headache, chronic progressive headache, hormone headache, for example.

A tension headache is a common type of primary headache. Patients that suffer from tension headache often state that pain is experienced in the forehead, in the back of the head and neck, or in both regions. It has been described as a tight feeling, as if their head were in a vise or as if someone was tightening a strap placed around the circumference of the head. Soreness in the shoulders or neck is common in persons complaining of tension headaches. In some persons, a mixed headache syndrome may occur, that is, a combination of tension and migraine headaches.

Some headaches are secondary headaches. For example, a cervicogenic headache is a headache which is due to a neck problem, such as an abnormality of the neck muscles, which can result from prolonged poor posture, arthritis, injuries of the upper spine, or from a cervical spine disorder. Typically, persons suffering cervicogenic headaches do not evidence pathological findings in x-rays or magnetic resonance imaging of the neck, further confusing the source or cause of their pain. It is supposed that the pain may stem from various structures in the upper part of the cervical spine. It is also theorized that the neck muscles may be involved in the pain generation, either primarily or secondarily. In particular cases, the pain can be reported as unilateral and may accompany a reduced range of neck motion. A strong indicator of a cervicogenic headache is that the headache can be elicited by palpation or pressure on muscles of the occiput (posterior portion of the head) or in the neck. Accordingly, in some instances, a cervicogenic headache can be precipitated by particular neck movements or by placing the head in a certain position.

A sinus headache causes pain in the front of the head and face and is due to inflammation of various sinus passages lying behind the cheeks, nose, and eyes. Pain associated with a sinus headache tends to be worse when a patient bends forward (i.e. moves face towards the floor, when upright) and when awakening from sleep. Postnasal drip, sore throat, and nasal discharge are commonly reported along with the head and facial pain.

Chronic progressive headaches (also known as traction or inflammatory headaches) are headaches that get worse and happen more frequently over time. One of the least common types of headache, chronic progressive headache is thought to be the result of an unspecified illness or disorder of the brain or skull.

Hormone headaches are particular headaches suffered by women associated with changing hormone levels that occur during menstruation, pregnancy, and menopause. Additionally, chemically induced hormonal changes, arising as a result of administration of birth control pills or injected synthetic progesterone, can also trigger headaches in some women.

A cluster headache is a headache that affects one side of the head (unilateral) and can also include tearing of the eyes and a stuffy nose. Cluster headaches occur repeatedly every day at approximately the same time for several weeks and then no longer occur. It has been postulated that cluster headaches may be related to a sudden release of histamine or serotonin by body tissues. Symptoms can include swelling under or around the eye, usually the same side as the head pain, as well as excessive tears and a red eye on the affected side. Rhinorrhea (runny nose) or nasal congestion (typically occurs on only one side of the nose, the same side as the head pain) can also manifest in sufferers of cluster headaches. The head pain of cluster headaches has been described as a steady, sharp or burning pain characteristically occurring on one side of the head, where the pain quickly worsens after its onset, peaking within about 10 minutes and last up to about 2 hours.

Migraine headaches are often associated with an intense pulsing or throbbing pain in one area of the head. In some persons, the head pain is accompanied by extreme sensitivity to light and sound, nausea, and vomiting. In particular sufferers, the onset of a migraine can be predicted because the migraine headache is preceded by an “aura,” that is, visual disturbances that appear as flashing lights, tingling in an arm or leg, or a temporary loss of vision. Migraine pain can be simply excruciating and may incapacitate a person for hours or even days. Migraine can be classified into chronic or episodic migraines. Persons suffering chronic migraines experience a migraine for fifteen or more days each month for more than three months. Persons suffering episodic migraines experience a migraine less than 15 days each month. In some instances, episodic migraines increase in frequency to daily or near-daily migraines, often without the usual features of a migraine, such as nausea or light sensitivity, giving rise to what is referred to as transformed, or evolved, migraines. Migraine treatment can include administration of antidepressants, anti-seizure medications or cardiovascular drugs, although use of these treatments by no means assures a person of complete relief. Depending upon the person, various triggers initiate the onset of a migraine headache. Exemplary triggers include lack of food or sleep, exposure to light or hormonal irregularities (in women). Anxiety, stress, or relaxation after stress, changes of weather, season, altitude level, barometric pressure or time zone (jet lag) have been known to prompt a migraine headache.

In many cases, triptans (tryptamine-based drugs) are used as abortive medication in the treatment of migraine and cluster headaches, that is, are administered to a patient as soon as the patient senses a headache coming on. While effective at treating specific individual headache episodes, they are neither a preventative nor a cure. Commonly prescribes triptans include sumatriptan (IMITREX, IMIGRAN) and naratriptan (AMERGE, NARAMIG) and zolmitriptan (ZOMIG).

Other methods for treating headaches have been disclosed, for example, utilizing Clostridial toxins. The current use of botulinum toxins in migraine treatment has involved injections into superficial muscles and subcutaneous tissue of the face and head.

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

About 50 picograms of a commercially available botulinum toxin type A (a purified neurotoxin complex available from Allergan, Inc., of Irvine, Calif. under the tradename BOTOX® in 100 unit vials) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacteria/Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 unit is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type* 8: *Experimental and Clinical Experience*, beginning chapter 6, pages 71-85 of "Therapy With Botulinum Toxin," edited by Jankovic, J. et al. (1994), Marcel Dekker, Inc. It has been known in the art that botulinum toxin type B can be administered efficiently and safely to humans in doses of 15,000 units or greater, even up to 25,000 units with repeated doses for up to 56 months. Kumar R and Seeberger L C., *"Long-term safety, efficacy, and dosing of botulinum toxin type B (MYOBLOC®) in cervical dystonia (CD) and other movement disorders"*, Mov Disord 2002; 17(Suppl 5):S292-S293. Botulinum toxin apparently binds with high affinity to cholinergic motor neurons, is translocated into the neuron, and blocks the release of acetylcholine. Additional uptake can take place through low affinity receptors, as well as by phagocytosis and pinocytosis.

Regardless of stereotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface. In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{2+}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G, cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). Almost twenty years ago, in 1989, a botulinum toxin type A complex was approved by the U.S. Food and Drug Administration for the treatment of blepharospasm, strabismus and hem ifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxin serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65.1999, and *Mov. Disord.,* 10(3):376: 1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule comprise the relevant neurotoxin complex) may act to provide stability against denaturation to the botulinum toxin molecule, and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain J Neurochem* 51(2); 522-527:1988)), CGRP, substance P, and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897). Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of* [3*H*] *Noradrenaline and* [3*H*]*GABA From Rat Brain Homogenate*, Experientia 44; 224-226: 1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype, only cleave a portion of the toxin produced. The exact proportion of nicked to unnicked molecules depends on the length of incubation and the temperature of the culture. Therefore, a certain percentage of any preparation of, for example, the botulinum toxin type B toxin, is likely to be inactive, possibly accounting for the known significantly lower potency of botulinum toxin type B, as compared to botulinum toxin type A (and thus the routine use of many thousands of units of botulinum toxin type B, as known in the art, see e.g. "*Long-term safety, efficacy, and dosing of botulinum toxin type B* (*MYOBLOC®*) *in cervical dystonia* (*CD*) *and other movement disorders"* Kumar R and Seeberger L C. Mov Disord 2002; 17(Suppl 5):S292-S293). The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3\times10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56;

80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2×$10^8$ $LD_{50}$ U/mg or greater; purified botulinum toxin type B with an approximately 156 kD molecular weight with a specific potency of 1-2×$10^8$ $LD_{50}$ U/mg or greater; and purified botulinum toxin type F with an approximately 155 kD molecular weight with a specific potency of 1-2×$10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition for use in accordance with the present disclosure.

As with enzymes generally, the biological activities of botulinum toxins (which are intracellular peptidases) is dependant, at least in part, upon their 3-dimensional conformation. Thus, botulinum toxin type A is detoxified by heat, various chemicals, surface stretching, and surface drying. Additionally, it is known that dilution of the toxin complex obtained by the known culturing, fermentation and purification to the much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. Botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 U of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks (*Neurology,* 48:249-53, 1997). It has been reported that botulinum toxin type A has been used in clinical settings as follows:

(1) about 75-125 U of BOTOX® somper intramuscular injection (multiple muscles) to treat cervical dystonia;

(2) 5-10 U of BOTOX® per intramuscular injection to treat glabellar lines (brow furrows) (5 units injected intramuscularly into the procerus muscle and 10 units injected intramuscularly into each corrugator supercilii muscle);

(3) about 30-80 U of BOTOX® to treat constipation by intrasphincteric injection of the puborectalis muscle;

(4) about 1-5 U per muscle of intramuscularly injected BOTOX® to treat blepharospasm by injecting the lateral pre-tarsal orbicularis oculi muscle of the upper lid and the lateral pre-tarsal orbicularis oculi of the lower lid;

(5) to treat strabismus, extraocular muscles have been injected intramuscularly with between about 1-5 U of BOTOX®, the amount injected varying based upon both the size of the muscle to be injected and the extent of muscle paralysis desired (i.e. amount of diopter correction desired);

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimis: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session;

(7) to treat migraine, pericranial (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three-month period following the 25 U injection.

It is known that botulinum toxin type A can have an efficacy for up to 12 months (*European J. Neurology* 6 (Supp 4): S111-S1150: 1999), and in some circumstances for as long as 27 months, when used to treat glands, such as in the treatment of hyperhidrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of effect of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and DYSPORT® available from Beaufour Ipsen, Porton Down, England. A botulinum toxin type B preparation (MYOBLOC®) is available from Solstice Pharmaceuticals of San Francisco, Calif.

A botulinum toxin has also been proposed for or has been used to treat otitis media of the ear (U.S. Pat. No. 5,766,605), inner ear disorders (U.S. Pat. Nos. 6,265,379; 6,358,926), tension headache, (U.S. Pat. Nos. 6,458,365 and 6,776,992), migraine headache pain (U.S. Pat. No. 5,714,468), sinus headache (U.S. Pat. No. 6,838,434), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805). U.S. Patent Application Publication 2007/0048334 A1, Ser. No. 11/211,311 and filed Aug. 24, 2005, discloses the use of a botulinum toxin to improve gastric emptying and/or treating gastroesophageal reflux disease (GERD) by administration to a patient's head, neck and shoulder muscles. It is known that a botulinum toxin can be used to weaken the chewing or biting muscle of the mouth so that self inflicted wounds and resulting ulcers can heal (Payne M., et al, Botulinum toxin as a novel treatment for self mutilation in Lesch-Nyhan syndrome, Ann Neurol 2002 September; 52(3 Supp 1):S157). U.S. Patent Application Publication 20050191321 A1, Ser. No. 11/039,506 and filed Jan. 18, 2004, discloses treating medication overuse disorders (MOD), by local administration of a Clostridial toxin. U.S. Patent Application Publication 20060104995 A1, Ser. No. 11/319,880 and filed Dec. 28, 2005 also discloses use of botulinum toxin at the head. U.S. Patent Application Publication 20050147626 A1, Ser. No. 10/964,898 and filed Oct. 12, 2004 discloses treating or preventing, by peripheral administration of a botulinum toxin to or to the vicinity of a trigeminal sensory nerve, a neurological disorder and/or a neuropsychiatric disorder. U.S. Patent Application Publication 20060171963 A1, Ser. No. 11/296,079 and filed Dec. 7, 2005 discloses a method for reduction of pain associated with a migraine headache, trigeminal autonomic cephalalgia and headache caused by a vascular condition by administering a therapeutically effective amount of a presynaptic neurotoxin around the nerve endings selected from the group consisting of: trigeminal nerve endings, occipital nerve endings and nasal parasympathetic nerve endings.

Additionally, a botulinum toxin may have an effect to reduce induced inflammatory pain in a rat formalin model. Aoki K., et al, Mechanisms of the antinociceptive effect of subcutaneous BOTOX®: Inhibition of peripheral and central nociceptive processing, Cephalalgia 2003 September; 23(7):649. Furthermore, it has been reported that botulinum toxin nerve blockage can cause a reduction of epidermal thickness. Li Y, et al., Sensory and motor denervation influences epidermal thickness in rat foot glabrous skin, Exp Neurol 1997; 147:452-462 (see page 459). Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44(Suppl 91):6), and foot dystonia (Rogers J., et al., Injections of botulinum toxin A in foot dystonia, Neurology 1993 April; 43(4 Suppl 2)). Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively).

Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocation domains.

Additionally, both the tetanus toxin and the botulinum toxins exhibit a high, specific affinity for ganglioside receptors on the surface of presynaptic cholinergic neurons. Receptor-mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., The Complete Sequence of Botulinum Neurotoxin Type A and Comparison with Other Clostridial Neurotoxins, J Biological Chemistry 265 (16); 9153-9158:1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

What is needed therefore is a patient-specific technique for treating a cranial pain, such as a headache pain, utilizing patient-specific landmarks. In a particular aspect, the present invention relates to the administration of a botulinum neurotoxin to a patient suffering from a headache/headache pain, where the location of administration of the botulinum toxin is in the vicinity of, and based upon, at least one suture line of the patient's skull, to thereby alleviate/treat the headache/headache pain of the patient.

SUMMARY

I have discovered a new, focused approach to treating headache pain which is patient-specific.

In one aspect, a method for treating a patient suffering from a headache is disclosed comprising the step of administering a Clostridial toxin to a nerve located in the vicinity of at least one suture line of the patient's skull, thus resulting in alleviation of at least one symptom of the headache. The method can include the step of determining the location of at least one suture line. Headache types that can be treated in accordance with the present disclosure can include, but are not limited to, a sinus headache, a tension headache, a migraine headache, a cluster headache and a cervicogenic headache, for example. In particular examples, the migraine that is treated can be an episodic migraine or a chronic migraine. The at least one suture line can be any suture line that the attending physician deems appropriate to administer the neurotoxin, and can be, but not limited to, a frontal suture, squamous suture, occipitomastoid suture, coronal suture, lambdoid suture and sagittal suture, for example.

In some embodiments, the Clostridial neurotoxin is a botulinum toxin, such as a botulinum toxin selected from the group consisting of botulinum toxin types A, B, $C_1$, D, E, F and G. In some preferred embodiments, the botulinum toxin is botulinum toxin type A and/or botulinum toxin type B.

In some examples, a method for treating a headache in a patient in need thereof comprises the steps of determining a location of cranial pain associated with the headache of the patient and determining the location of at least one suture line of the patient that is most proximal to the location of headache pain. After determining the location of the at least one suture line most proximal to the location of cranial pain, a Clostridial neurotoxin is administered to the patient, for example in a continuous uninterrupted fashion, along the length of and substantially superimposed in the vicinity of the at least one suture line. As above, the Clostridial neurotoxin can be a botulinum toxin selected from the group consisting of botulinum toxin types A, B, $C_1$, D, E, F and G.

In particular embodiments, the administration step includes a step of inserting a needle of a syringe containing a botulinum toxin, such as a botulinum toxin type A or B, for example, at a penetration point, and positioning the needle along the at least one suture line so that the botulinum toxin type A is administered linearly along the at least one suture. Exemplary sutures that can be the at least one suture are, but not limited to, the frontal suture, squamous suture, coronal suture, lambdoidal suture, occipitomastoid suture and sagittal suture, for example. In particular instances, a further step of repositioning the needle, utilizing the same penetration point, to direct linear botulinum toxin distribution along a second suture line can also be executed.

In some embodiments, the method for alleviating a headache pain can comprise subdermally administering a botulinum toxin type A to a patient in need thereof, where the botulinum toxin type A is administered to the patient in the vicinity of a suture line and the administration alleviates the headache pain within seven days. In some examples, the headache pain remains alleviated for between about 2 to about 6 months or even longer.

The Clostridial neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. "U" is an abbreviation for "units." More preferably, the neurotoxin is administered in an amount of between about $10^{-1}$ U/kg and about 15 U/kg. In a particularly preferred method within the scope of the present invention, the botulinum neurotoxin is locally administered in an amount of between about 1 U/kg and about 10 U/kg. In a clinical setting it can be advantageous to administer from 1 U to 3000 U of a neurotoxin, such as botulinum toxin type A or B, linearly along and in the vicinity of the at least one suture to effectively treat a headache. In particular examples, administered botulinum toxin can be from about 1 unit to about 25,000 units, depending upon the serotype of botulinum neurotoxin utilized, of course, that is, an attending medical practitioner clearly and in no way considers administration of a lethal dose of a particular serotype (a non-working embodiment) to be a therapeutic dose. Beneficial non-lethal botulinum toxin doses, based on the particular serotype of neurotoxin being utilized and known to those of ordinary skill in the art (as evidenced in the art) are utilized, of course.

In a particular method, the administration step of a botulinum toxin type A comprises utilizing a needle inserted through cranial subcutaneous tissue, cranial muscle and aponeurotic fascia and in the vicinity and along the suture line of the patient, and then withdrawing the needle gradually along the suture line while at the same time delivering the botulinum toxin type A, in order to provide linear, subcutaneous distribution of the botulinum toxin type A along the suture line (such as, for example, a frontal, squamous, coronal, lambdoidal and sagittal suture line). In some embodiments, one penetration point is utilized to administer the botulinum toxin, such as a botulinum toxin type A or B, along at least two suture lines. In still other embodiments, more than one penetration point is utilized to administer the botulinum toxin along the length of the same or different suture lines.

"Botulinum toxin" means a botulinum neurotoxin as either pure toxin (i.e. about 150 kDa weight molecule) or as a complex (i.e. about 300 to about 900 kDa weight complex comprising a neurotoxin molecule and one or more associated non-toxic molecules), and excludes botulinum toxins which are not neurotoxins such as the cytotoxic botulinum toxins C2 and C3, but includes recombinantly made, hybrid, modified, and chimeric botulinum toxins. "Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Alleviating" means a reduction in the occurrence of a headache related symptom. Thus, alleviating includes some reduction, significant reduction, near total reduction, and total reduction of a headache related symptom. An alleviating effect may not appear clinically for between about 1 to about 7 days after administration of a Clostridial neurotoxin to a patient.

Exemplary symptoms can be particular to the type of headache experienced, such as, for example, a person suffering from a tension headache can have pain or discomfort in the head, scalp, or neck that is usually associated with muscle tightness in these areas. The person can have dull, pressure-like pain that is generalized (all over the head, not just in one point or one side), worse in the scalp, temples or back of the neck, the feeling of a tight band or vise on the head. In a cluster headache, symptoms can affect one side of the head (unilateral) and may involve tearing of the eyes and a stuffy nose, as well as beginning 2 to 3 hours after falling asleep and described as a steady, sharp pain or a burning or boring pain occurring on one side of the head and/or in and around one eye. For migraines sufferers, exemplary symptoms can include nausea, vomiting, and localized pain to particular areas of the head, visual disturbances (aura) in one or both eyes (including seeing zigzag lines, flashing lights, temporary blind spots), sensitivity to bright light and blurred vision. Additional symptoms of migraine headache can include loss of appetite, chills, increased urination, increased sweating, and swelling of the face, irritability, and fatigue. Migraine pain is often described as a "pounding" feeling that starts on one side of the head and sometimes spreads to the other side of the head. In some patients, migraine headaches start on the same side of the head each time and can include pain behind the eye or in the back of the head and neck.

"About" means approximately or nearly and in the context of a numerical value or range set forth herein means +/−10% of the numerical value or range recited or claimed.

When the term "in the vicinity of" is utilized herein, it means that which is referred to is at or within about 1.5 cm, more preferably at or within about 1.0 cm and most preferably at or within about 0.5 cm of a specified referenced location, e.g. when botulinum toxin is administered in accordance with the present disclosure, it is administered within the vicinity of at least one suture line of the patient, i.e. at or within about 1.5 cm, more preferably at or within about 1.0 cm or most preferably at or within 0.5 cm away from the suture line referenced.

A "therapeutically effective" amount of a botulinum neurotoxin is a dosage sufficient to provide alleviation of at least one symptom associated with a headache for at least one week, more preferably one month, most preferably for approximately 4 to 9 months or longer and up to 5 years. Dosing can be single dosage or cumulative (serial dosing), and can be readily determined by one skilled in the art. Neurotoxin, such a botulinum toxin, can be delivered serially (i.e., one time per month, one time per every six months) such that an optimal amount of toxin is administered in accordance with the severity of the headache treated and beneficial results are maintained. Such a dosage schedule is readily determined by one skilled in the art based on, e.g., patient size, the neurotoxin selected, the condition to be treated, severity of the disorder and other variables known in the art.

Various methods of administration can be utilized to administer compositions useful in practicing the methods disclosed herein. In one instance, administration of a botulinum toxin in the vicinity of at least one suture line is achieved by subdermal injection of a composition containing botulinum toxin, utilizing a needle, as described in more detail below, for example. An additional exemplary administration method that can also be utilized is via a transdermal route, i.e. to administer the botulinum toxin in accordance with the teachings/parameters herein disclosed (utilizing skull suture lines) without using a needle, that is, via topical administration (e.g. Published U.S. Patent Application No. 20040009180 A1, Ser. No. 10/194,805 filed Jul. 11, 2002, herein incorporated by reference in its entirety, discusses topical toxin administration). Administration of botulinum toxin transdermally is known in the art, as is needleless administration, which is also contemplated as a method of administration useful in accordance with the teachings of the present invention.

"Treating" means to alleviate (or to eliminate) at least one symptom of a headache, either temporarily or permanently.

"Patient" means a human or non-human subject receiving medical or veterinary care. Accordingly, as disclosed herein, the compositions may be used in treating any animal, such as mammals.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

My invention will be better understood by reviewing the drawings accompanying this specification, which are not drawn to scale and are for illustrative/exemplary purposes.

DESCRIPTION

Figure 1:
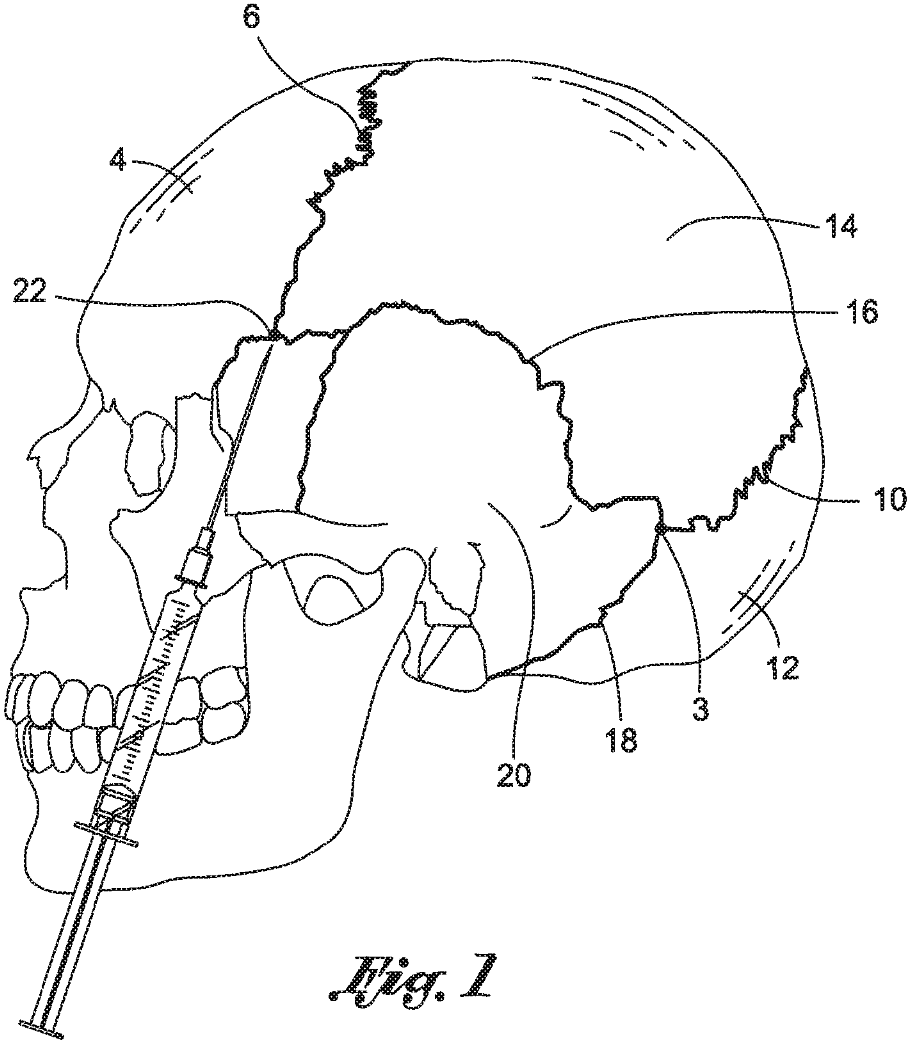
FIG. 1 is a left-side side view of a human skull showing the various bones that comprise a skull, exemplary needle penetration points, a syringe about to be inserted, as well as exemplary borders between bones (suture lines)

In accordance with the present invention, botulinum neurotoxin is administered to a patient that suffers from a headache pain. More particularly, the instantly disclosed method is focused and patient-specific, allowing a medical practitioner to better target and alleviate a patient's headache pain utilizing specifically localized and administered botulinum toxin, for example.

It has come to my attention that in some instances, migraine headaches involve increased activity of trigeminal and occipital nerves at the level of the meninges. Pain associated with migraine headaches result from a sensitization of these nerve endings, which are then able to detect cerebral spinal fluid (CSF, the clear the fluid that surrounds the brain and spinal cord serving as a cushion to protect both brain and spine from injury) pulsations and also lead to meningeal blood vessel changes, which propagate a migraine cascade.

Nerves supplying the meninges have traditionally been considered as intra-cranial. This involves branches of the first division of the trigeminal nerve and high cervical nerve roots. Based on my neurology practice, I believe that headache pain, such as migraine headache pain for example, predominantly involves meningeal nociceptive nerves and that these nerves traverse the skull to reach the meninges, the most likely entry point being the suture lines, as this is a natural break in the bony casement of the brain.

Additionally, intra-cranial branches of the first division of the trigeminal nerve and high cervical nerve roots supply the meninges but also exit the skull to supply the periosteum (the thin layer of dense, irregular connective tissue membrane that covers the outer surface of the cranium) and scalp. The predominant nerve fibers that travel across the skull either from the scalp surface to the meninges or from the meninges to the scalp are unmyelinated C fibers (unmyelinated fibers from about 0.4 to about 1.2 micrometers in diameter which conduct nerve impulses at a velocity of about 0.7 to about 2.3 meters per second).

Interestingly, skull nerve penetration points appear to be maximal at areas that correspond to the suture lines, that is, the borders at which the skull's bony plates come together. Accordingly, the instant method utilizes localized botulinum toxin administration that is based upon the location of at least one of the patient's suture lines as a guide to where botulinum neurotoxin is to be administered. This suture line-based administration technique allows delivery of a medicament, containing a botulinum toxin for example, to the bony surface of the skull at the exact point where the nerve endings are accessible. Thus a lower dose of medicament to treat a headache pain is required and in addition, potential side effects, such as unwanted muscle weakness, are limited.

Exemplary, commercially available, botulinum toxin containing compositions include, but are not limited to, BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), DYSPORT® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use) which can be used at about 3 to about 4 times the amounts of BOTOX® as set forth herein in each instance, and MYOBLOC® (an injectable solution comprising botulinum toxin type B, human serum albumin, sodium succinate, and sodium chloride at about pH 5.6, available from Solstice Neurosciences, Inc., South San Francisco, Calif.) which can be used at about 30 to about 50 times the amounts of BOTOX® as set forth herein in each instance, as known in the art. XEOMIN® (a 150 kDa botulinum toxin type A formulation available from Merz Pharmaceuticals, Potsdam, Germany) is another useful neurotoxin which can be used at about 1 to about 2 times the amounts of BOTOX® as set forth herein in each instance.

In general, a patient is examined by careful palpation of the skull. The suture lines are mapped out as follows: coronal, squamous, sagittal, and lambdoid sutures. A Clostridial toxin, such as a botulinum toxin, is injected along the suture lines by infiltration. In one administration method, needles of various sizes can be utilized, such as, for example, 1.5 inches long and of 30, 27 or even 25 gauge can be used. Preferably, the needle selected is at least 1 inch long. The needle is inserted through the subcutaneous tissue, through the muscle, and through the aponeurotic fascia of the scalp. The needle does not penetrate the periosteum and can be inserted to its full length along the targeted suture line and then botulinum toxin, for example, is delivered by gradually withdrawing the needle along the targeted suture line while the plunger of the syringe is depressed. This technique provides and allows a substantially linear distribution of botulinum toxin along the suture line. (see FIGS. 1-3, for example).

A concentrated solution of botulinum toxin is preferably used, such as, for example and in the case of utilizing BOTOX® (botulinum toxin type A), 1 cc of normal unpreserved saline per 100 unit vial of BOTOX® (although 2 cc and 4 cc dilutions per 100 units of BOTOX® could also be utilized). In one embodiment, this is completed along coronal, squamous, sagittal, and lambdoid sutures. The penetration point of the needle can be done at just 4 sites (exemplified in FIG. 1 as needle penetration point 22 (one on each side of the head), needle penetration point 5 in FIG. 5 and needle penetration point 1 in FIG. 6): the needle can be directed along the suture lines and then re-directed through the same penetration point in each location. For example the left coronal suture line and the left squamous suture line can be treated with a penetration point at the apex of the juncture of the left coronal and squamous sutures. This method of administration is termed: a suture line administration technique. To date this technique has not been described or published.

Figure 2:
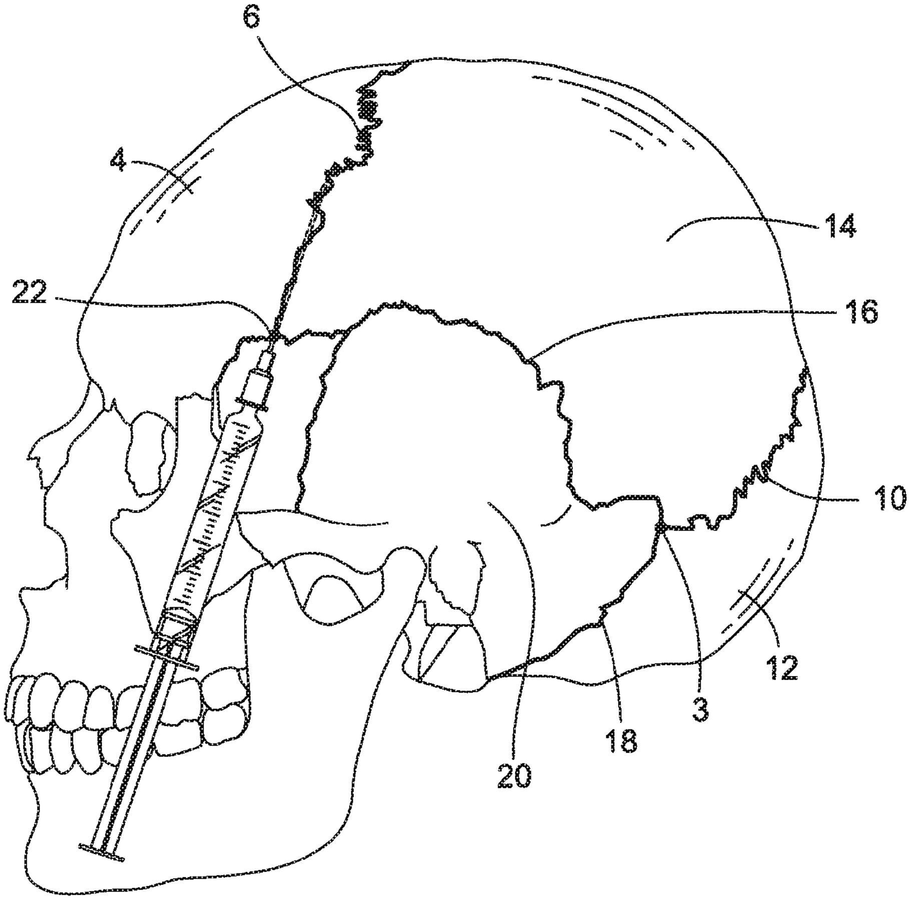
FIG. 2 is a left-side side view of a human skull depicting the syringe and needle inserted to its length alongside and in the vicinity of coronal suture.

Turning to FIG. 1, an exemplary left-side side view of a human skull is depicted, showing various bony plates that comprise the skull. These include the frontal bone 4, the parietal bone 14, the temporal bone 20, sphenoid bone 21 and the occipital bone 12. The edges at which these bony plates meet are held together by cranial sutures. These sutures are held together mainly by Sharpey's fibers, which grow from each bone plate into the adjoining bone plate. In the skull, the main function of Sharpey's fibres is to bind the cranial bones in a firm but moveable manner. These fibers are most numerous in areas where the bones are subjected to the greatest forces of separation and are accompanied by an arteriole and one or more nerve fibers. Retzlaff, E W; Mitchell F L, Upledger J E (1982-3). "Efficacy of Cranial Sacral Manipulation: The Physiological Mechanism of the Cranial Sutures". *J Soc. Osteopaths* (12). ISSN 0308-8766.

Various exemplary sutures can be seen in FIG. 1. For example, the coronal suture 6, which is at the junction of the frontal 4 and parietal 14 bones, is shown, as well as the squamous suture 16, at the junction between the parietal 14 and temporal 20 bones, and the lambdoid suture 10, at the junction between the parietal 14 and occipital bone 12 and the occipitomastoid suture 18, the cranial suture between the occipital bone and the mastoid portion of the temporal bone. These are some exemplary sutures that are utilized in accordance with teachings provided herein, where botulinum toxin is administered to a nerve located in the vicinity of at least one suture line of the patient's skull, whereby the administration alleviates at least one symptom of the headache. As detailed previously, administration can substantially follow along the length of the suture line, e.g. at or up to about 1.5 cm away, more preferably at or up to about 1.0 cm, most preferably at or up to about 0.5 cm from the suture line referenced and utilized as a guide for botulinum toxin administration in accordance with the instant disclosure. Dotted outlining provided/indicated in the FIGs represents location of the indicated object (e.g. needle, administered toxin along a suture line(s)) that is below the skin surface.

Figure 3:
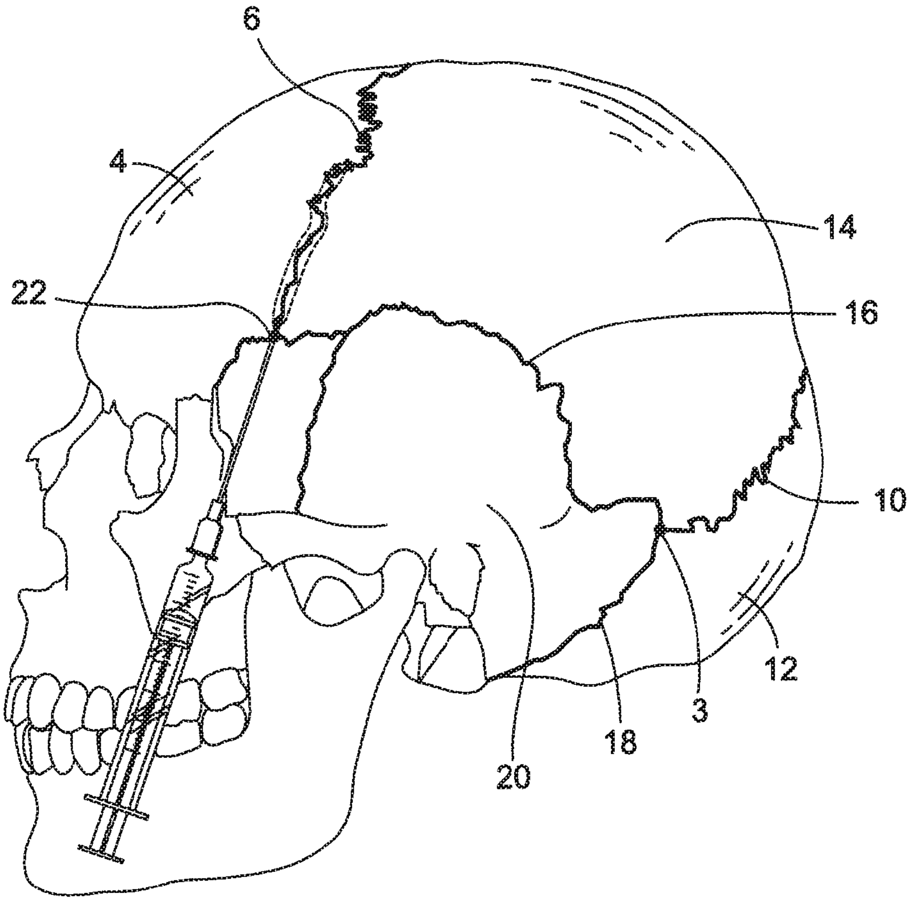
FIG. 3 is a left-side side view of a human skull depicting the syringe and needle being withdrawn as the plunger is depressed, leaving a trail of administered neurotoxin in the vicinity of and along the coronal suture.
Figure 4:
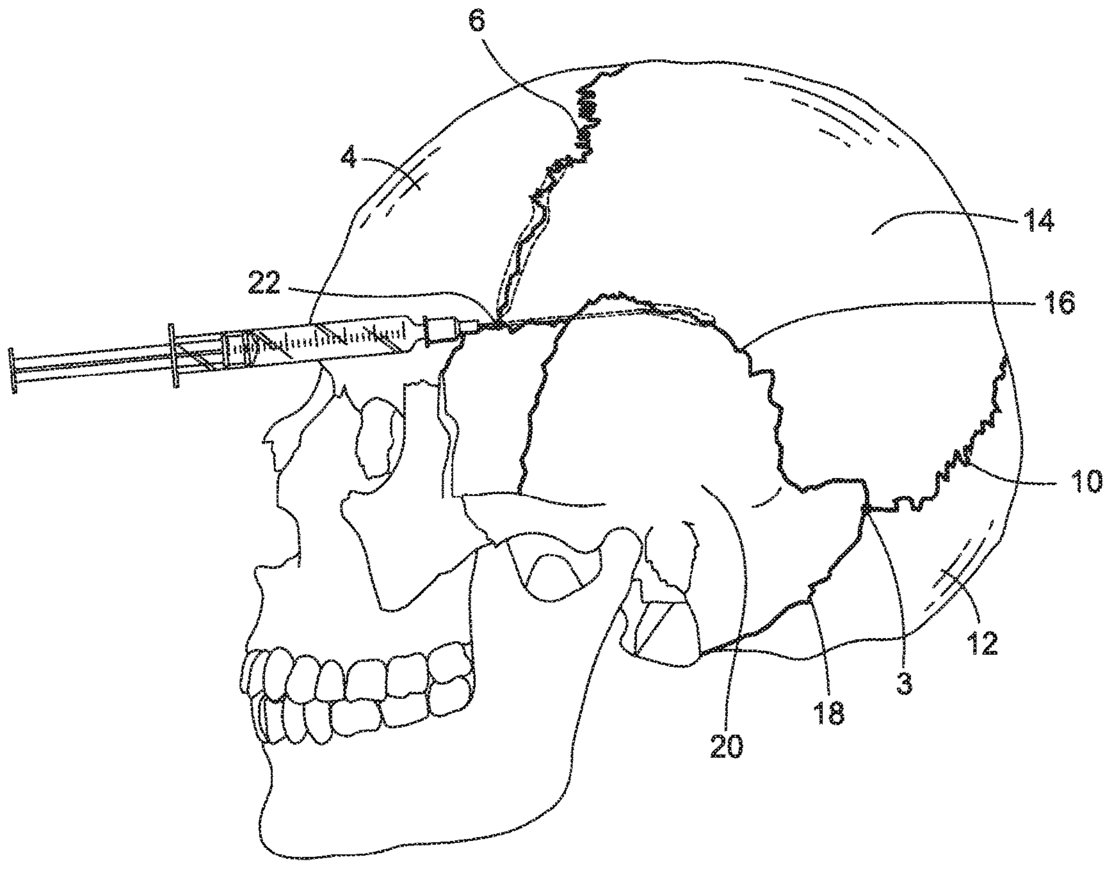
FIG. 4 is a left-side side view of a human skull showing the syringe re-oriented, utilizing the same needle penetration point shown in FIGS. 1-3 and administering a neurotoxin along the squamous suture in accordance with the present disclosure.

In accordance with one aspect of the invention, botulinum neurotoxin administration is achieved by insertion of an appropriately sized needle (e.g. 27 gauge) at a needle penetration point, such as needle penetration point 22 in FIG. 1. In this example, needle penetration point 22 is at the junction of coronal suture 6 and squamous suture 16. This location provides access to the length of two suture lines, for example upward along the coronal suture 6, as well as along the squamous suture 16, by utilizing a single needle penetration point 22. In this example, once the needle of the syringe (containing a botulinum toxin) is inserted at needle penetration point 22, it is then inserted to it's full lengthen (or less than its full length, if so desired) upwardly and along coronal suture 6, and then once at the end if its insertion (FIG. 2), the toxin is delivered by gradually withdrawing the needle along the coronal suture 6 while at the same time the plunger of the syringe is depressed, thus providing a linear distribution of botulinum toxin along coronal suture 6 (FIG. 3). Once the tip of the needle reaches needle penetration point 22 (end of withdrawal), the needle is re-oriented to travel and be inserted along squamous suture 16, the needle once again inserted to its full length (or less than its full length, if so desired) along squamous suture 16, and then once again when at the end if the needle's insertion, the toxin is delivered again by gradually withdrawing the needle along the squamous suture 16 while at the same time depressing the plunger of the syringe, thus providing a linear and continuous distribution of botulinum toxin along squamous suture 16 (FIG. 4) thus requiring only a single needle penetration point to access more than one suture line.

Figure 5:
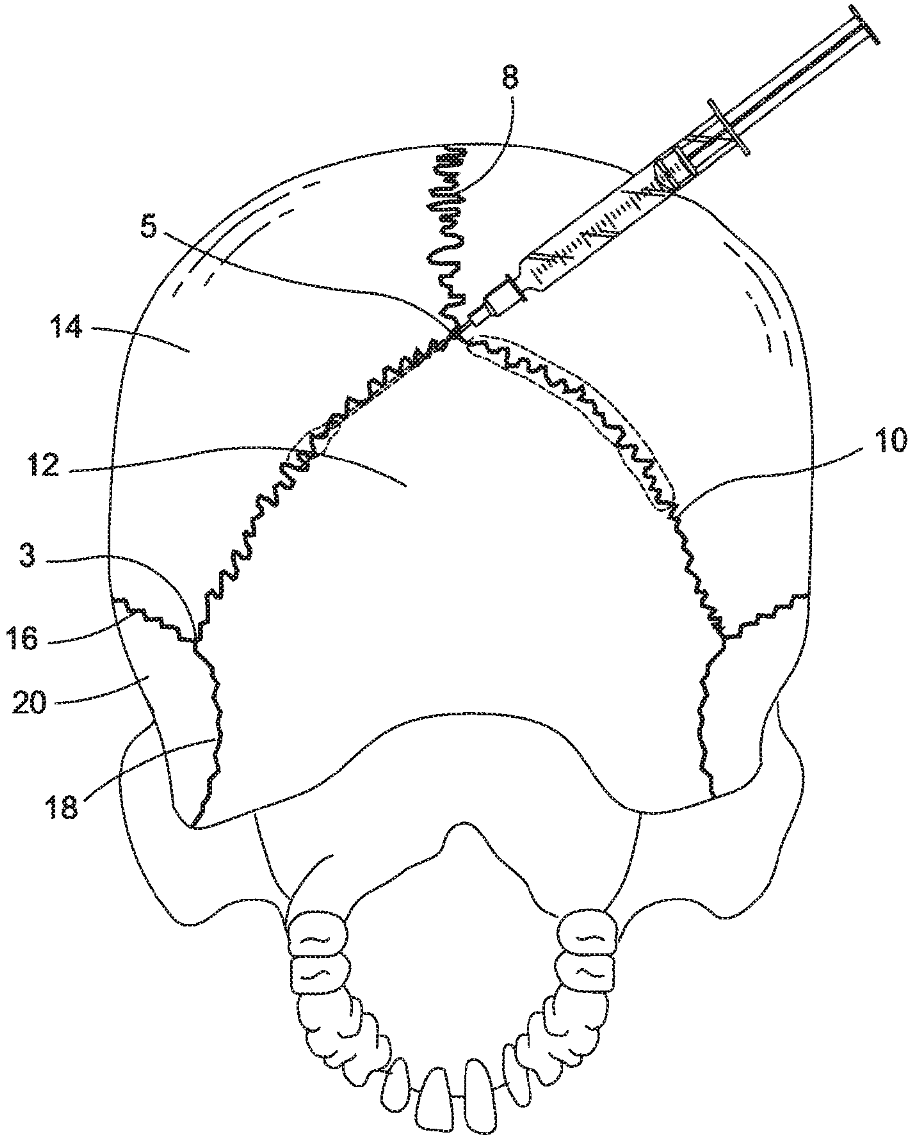
FIG. 5 is a rear-view of the back of a human skull, depicting another exemplary needle penetration point and administered neurotoxin and a syringe in the process of depositing neurotoxin along the lambdoid suture in accordance with the teachings provided herein.

In another aspect, FIG. 5 depicts a rear-view (dorsal view) of the back of a human skull, showing an exemplary second needle penetration point 5, at the junction of the sagittal suture 8 and lambdoid sutures 10 that form at the border of the parietal bones 14 and the occipital bone 12. In some instances, a person may complain of a headache pain, such as a migraine headache, that results in pain felt at the back of the patient's head. In one example, a botulinum toxin can be administered to that patient along and in the vicinity of the specific suture lines found at the back of the patient's head. Locating suture lines can be accomplished by a medical provider utilizing various methods, such as, but not limited to, careful palpitation, use of ultrasound, CT-fluoroscopy and radioisotope bone scans.

For instance and as exemplified in FIG. 5, a needle of a syringe containing a medicament, such as botulinum neurotoxin, is inserted at needle penetration point 5, and is then inserted to it's full lengthen downwardly and along the left "leg" of the lambdoid suture 10 and then once at the end if its insertion, the botulinum toxin is delivered by gradually withdrawing the needle along the left "leg" of the lambdoid suture 10 while at the same time the plunger of the syringe is depressed, thus providing a linear distribution of botulinum toxin along the left "leg" of the lambdoid suture 10. The same procedure is then performed, this time along the right "leg" of the lambdoid suture 10, resulting in the administration of a therapeutic amount of botulinum toxin in the form of an inverted "V" at the back portion of the patient's head.

If needed, and by still utilizing the same needle penetration point 5 (thus minimizing tissue trauma to the patient) a therapeutic amount of a botulinum neurotoxin can be administered along the top of the skull and along the line of and in the vicinity of the sagittal suture 8. Administration in the vicinity of and along sagittal suture 8 can be done if the patient complains of a headache pain that is at the top of their head. Here the needle of the syringe is inserted (or re-oriented, if already utilized to administered toxin along the lambdoid suture 10) at needle penetration point 5, and is then inserted to it's full lengthen upward/forwardly toward the face/front of the patient and along the sagittal suture 8 and then once at the end if its insertion the botulinum toxin is delivered by gradually withdrawing the needle along sagittal suture 8, while at the same time the plunger of the syringe is depressed, thus providing a linear distribution of botulinum toxin along the sagittal suture 8. If administered along with botulinum toxin to the "right" and "left" "leg" of the lambdoid suture 10 (right and left of the sagittal suture 8), the administration of the therapeutic amount of botulinum toxin is provided roughly the form of an inverted "Y" at the back portion of the patient's head when observed from the depicted perspective in FIG. 5.

Figure 6:
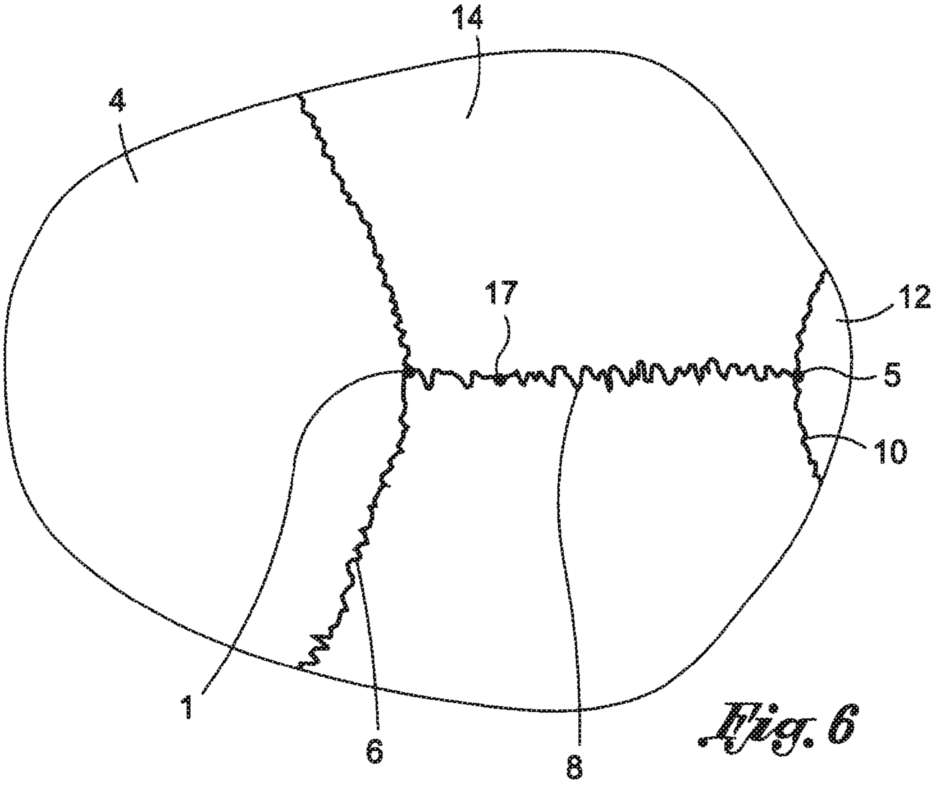
FIG. 6 is a top view of an exemplary human skull, showing various suture lines and needle penetration points, amendable to neurotoxin administration as disclosed herein.

In some instances, patients can present with a headache pain that is localized about the top of their head. In such cases, the attending physician can decide to administer a therapeutically effective amount of a botulinum toxin along the coronal suture 6 and/or the sagittal suture 8. As depicted in FIG. 6 (a top view of an exemplary human skull, showing various suture lines), these sutures come together at another needle penetration point 1, from which the coronal suture 6 on the left and right side of the skull can be accessed, as well as the sagittal suture 8 running from needle penetration point 1 to needle penetration point 5. As described previously, the needle of a syringe containing a medicament, such as a botulinum neurotoxin, can be inserted at needle penetration point 1, and is then inserted to it's full length downwardly (or less than its full length, if so desired) and along the left side of the skull along and in the vicinity of coronal suture 6, and then once at the end if its insertion, the botulinum toxin is delivered by gradually withdrawing the needle along the coronal suture 6 while at the same time the plunger of the syringe is depressed, thus providing a linear distribution of botulinum toxin along the left side and top of the patient's skull and in the vicinity of coronal suture 6. Utilizing the same needle penetration point 1, the needle is then repositioned to be advanced along the right side of the patient's skull, to its full length downwardly (or less than its full length, if so desired) and along the right side in the vicinity of and along coronal suture 6. Once again botulinum toxin is delivered by gradually withdrawing the needle along the coronal suture 6 while at the same time the plunger of the syringe is depressed, thus providing a linear distribution of botulinum toxin along the right side and top of the patient's skull in the vicinity of coronal suture 6. If desired, botulinum toxin can be administered along the top-midline portion of the patient's skull, along and in the vicinity of the sagittal suture 8 utilizing needle penetration point 1, administering the botulinum toxin in the manner described above, so as to deliver a linear distribution of botulinum toxin along and in the vicinity of sagittal suture 8.

Of course, there is no need to limit insertion of a needle to a point that is a junction between suture lines. It is further contemplated that in some instances an insertion point can be in the vicinity of and along any part of a suture line and not just at a location where two or more suture lines meet. For example and as exemplarily depicted in FIG. 6, perhaps a patient presents with a headache pain that is running along the midline of their head and starts at a topmost portion of the skull. In such an instance, a needle penetration point may be selected that is in the vicinity of a suture line, such as sagittal suture 8 and a needle is injected at a needle penetration point 17, whereby the needle is advanced forwardly and along sagittal suture 8, toward the forehead/front. The needle may be stopped at the juncture of the coronal suture 6 and the sagittal suture 8 (i.e. needle penetration point 1) or can be advanced further past needle penetration point 1 and into the area above frontal bone 4, where there is no suture line. The botulinum toxin is delivered by gradually withdrawing the needle along the sagittal suture 8 while at the same time the plunger of the syringe is depressed, thus providing a linear distribution of botulinum toxin along the top of the patient's skull and in the vicinity of sagittal suture 8.

In some instances, patients may complain of headache pain that is localized at the forehead. In such instances, botulinum toxin can be administered to the vicinity of and along the patient's coronal suture, for example and in accordance with the teachings herein provided.

An example of a commercially available botulinum toxin type A is BOTOX®. Each vial of BOTOX® contains 100 units of *Clostridium botulinum* toxin type A (purified), 0.5 mg albumin (human), and 0.9 mg sodium chloride in a sterile, vacuum-dried form without a preservative. One unit corresponds to the calculated median lethal intraperitoneal dose ($LD_{50}$) in mice. Preferably, the vials are stored in a freezer between −20 degrees Centigrade and −5 degrees Centigrade before use. Reconstitution is with 0.9% sterile saline (without preservatives) for injection.

Examples of Clostridial toxins within the scope of the present invention include neurotoxins made by *Clostridium botulinum, Clostridium butyricum* and *Clostridium baratti* species. In addition, the botulinum toxins used in the methods of the invention may be a botulinum toxin selected from a group of botulinum toxin types A, B, $C_1$, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection.

The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient in accordance with the methods disclosed herein.

The amount of a botulinum toxin selected for local administration in the vicinity of and along a suture line, according to the present disclosed invention, can be varied based upon criteria such as the severity of the headache pain or type of headache being treated, solubility characteristics of the neurotoxin toxin chosen as well as the age, sex, weight and health of the patient. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, and published by McGraw Hill).

The following non-limiting examples provide those of ordinary skill in the art with specific selection and treatment methods within the scope of the present invention, and are not intended to limit the scope of the invention. In the following examples, various modes of non-systemic administration of a Clostridial neurotoxin are carried out that are patient-specific and carried out by, for example, injection or by transdermal application. It is further contemplated that implantation of a controlled release implant in accordance with the teachings disclosed herein, namely within the vicinity and along at least one suture line that is at or proximal to a headache pain, can also provide beneficial therapeutic effect.

Example 1

A 22 year old woman (occupation actress) presents with a history of headaches that are consistent with migraine. She has headaches on at least half the days of the month. These are felt over the fronto-temporal regions of the head bilaterally and to a lesser extent over the occipito-parietal areas. The pain is throbbing in nature. During the headache the scalp feels tender in these locations. Her headaches are associated with significant depression. She has failed to respond to numerous medications including treatment with botulinum toxin injected into the procerus, corrugator, frontalis, temporalis and occipitalis muscles.

After signing a consent form she is treated with botulinum toxin using the following injection technique.

Utilizing botulinum toxin type A (BOTOX®), 100 units is reconstituted with preservative free normal saline using 1 cc per 100 units. Two 1 cc syringes are prepared with 50 units of botulinum toxin type A in each. The skull suture lines are palpated and mapped out. The hair is parted and the scalp cleaned with alcohol. Using a 1.5 inch, 27 gauge needle, the needle is inserted substantially parallel to the skull surface, along the suture lines. The first injection point is at the suture apex on the left side of her head, where the coronal suture 6 and squamous suture 16 meet (as exemplified as needle penetration point 22 in FIG. 1). The needle is inserted upwardly first along the coronal suture 6 and then gradually withdrawn as the plunger is depressed, so that 15 units are delivered in a linear and continuous fashion along the coronal suture 6 on the left side of her head. The needle is then re-directed along the squamous suture 16 line, using the same penetration point and botulinum toxin type A is similarly administered. This is repeated on the right side of her head using the same method, so that a total of 60 units of botulinum toxin type A (BOTOX®) is administered. Care is taken not to penetrate the periosteum, as this is known to cause an acute headache. The patient tolerates the procedure well and returns to clinic 6 weeks later. She now retains full movement of the muscles of expression and is able to continue acting. Her headaches are lessened in frequency and intensity and her scalp is less tender. In addition she notes that her depression is alleviated.

Example 2

A 37 year old chief financial officer arrives at his doctor's office complaining of headaches that have wracked his head about every three days over the past two months. The patient states that he experiences pain in the forehead and in the back of the head. The pain is described as a tight feeling, as if his head were in a vise. The physician decides to administer botulinum toxin type A (DYSPORT®) in the vicinity of and along the patient's coronal suture 6 and the lambdoid suture 10. Utilizing botulinum toxin type A (DYSPORT®), 500 units is reconstituted with 1 mL of sodium chloride injection B.P. (0.9%). Two 1 cc syringes are prepared with 250 units (0.5 mL solution) of botulinum toxin type A in each. The skull suture lines, here the patient's coronal suture 6 and the lambdoid suture 10 are palpated and mapped out. The hair was parted and the scalp cleaned with alcohol. Using a 1.5 inch, 27 gauge needle, the needle is inserted substantially parallel to the skull surface, at needle penetration point 1 (Exemplified in FIG. 3) and laterally down along first the left and then right side of the skull, along the coronal suture 6. As previously described, the needle, in each instance (left and right side) is gradually withdrawn as the plunger is depressed, so that 125 units of botulinum toxin type A is delivered in a linear and continuous fashion along and in the vicinity of the coronal suture 6, to each the left and right of needle penetration point 1.

Similarly, the patient's lambdoid suture 10 is mapped out, the hair parted and a needle of a syringe containing 250 units is inserted at penetration point 5 (exemplified in FIG. 2) substantially parallel to the skull surface and downwardly along the left side of the patient's skull, along lambdoid suture 10 to its full needle length and then is gradually withdrawn as the plunger is depressed, so that 125 units of botulinum toxin type A is delivered in a continuous, linear fashion along and in the vicinity of lambdoid suture 10 on the left side, and then the needle is then re-directed along the lambdoid suture 10 line, this time to the right side of the skull, using the same penetration point 5, and 125 units of botulinum toxin type A is similarly administered linearly and continuously along the right lambdoid suture 10 line.

The patient returns to the doctor's office two months later for a follow-up session. The patient states that since receiving the botulinum neurotoxin administration along his suture lines, he has experienced only two headaches in the two months and these two headaches were of shorter duration and intensity when compared to his previously experienced headaches.

Example 3

A 26 year old bartender presents at her doctor's office complaining of monthly headaches that she has experienced for the last 4 years. While she typically utilizes various analgesics (aspirin, ibuprofen etc . . . ), it is apparent to her that such an approach is turning out to be less and less effective as every month passes. Previous treatment with botulinum toxin type A injected into the frontalis, and temporalis muscles had not been effective. After taking down a thorough patient history and conducting a physical examination, her doctor comes to the conclusion that the patient is suffering from hormonal headaches, that is, the headache appears to coincide with the arrival of her menses.

By asking the patient where her headache pain is typically localized, the doctor learns that the pain is localized at the top and at the sides of her head. Accordingly, the doctor decides to administer a botulinum toxin in accordance with the teachings of the present disclosure. The doctor proceeds to administer a botulinum toxin type B (MYOBLOC®) in the vicinities of and along the patient's sagittal suture 8 and squamous suture 16 lines. The patient's sagittal suture 8 line is mapped out, along with her squamous suture 16 lines (one on each side of her head) and her scalp is cleaned with rubbing alcohol. Using a 2 inch, 27 gauge needle, the needle is inserted substantially parallel to the skull surface, at needle penetration point 22 (for example) on the left side of the patient's head, and back along and in the vicinity of squamous suture 16, avoiding penetration of the periosteum. Once the needle is inserted to about its full length, the needle is gradually withdrawn as the plunger is depressed, so that 500 units of botulinum toxin type B is delivered in a linear continuous fashion along and in the vicinity of squamous suture 16. The same administration is performed on the right side of the patient's head, where another 500 units is administered linearly and continuously along the squamous suture 16 on the right side of the skull. Similarly, the doctor administers 1000 units of a botulinum toxin type B along and in the vicinity of the sagittal suture 8, by inserting the needle of the syringe at penetration point 17 (as exemplarily depicted in FIG. 3), whereby the needle is inserted substantially parallel to the skull surface and pushed forward toward the patient's forehead/front, and once the needle is inserted to about its full length, it is again gradually withdrawn as the plunger is depressed, so that 1000 units of botulinum toxin type B is delivered in a linear continuous fashion along and in the vicinity of sagittal suture 8. During a follow-up session 6 months later, the patient reports that she no longer experiences hormonal headaches that coincide with her menstrual periods. Two months after her follow-up session, she returns to her doctor's office to report that headache coinciding with her menses has returned, and she is administered another round of botulinum toxin type B injections as before, which alleviate and provides relief for the patient for approximately another 6 months.

Example 4

A 54 year old housewife reports to her doctor that ever since her husband's retirement she is currently beset with cluster headaches that are associated with an intense pulsing/throbbing pain on the left side of her head and around her left ear, as well as a stuffy nose and teary left eye. It is decided that she receive 100 units of a botulinum toxin type A (BOTOX®) along and in the vicinity of her squamous suture 16 on the left side of her head. 100 units of botulinum toxin type A (BOTOX®) is reconstituted in 0.5 ml of non-preserved saline. The patient's left squamous suture 16 is mapped out and marked, and needle penetration point 22 (exemplified in FIG. 1) is cleaned with alcohol. The needle (1.5 inch, 30 gauge) of the syringe containing the botulinum toxin type A is inserted at needle penetration point 22, positioned and inserted rearwardly and through cranial subcutaneous tissue, cranial muscle and aponeurotic fascia, substantially parallel to the skull and in the vicinity of and along the left squamous suture 16 line of the patient. Once the needle's length is fully inserted, the needle is withdrawn gradually along the squamous suture 16 line, while at the same time the syringe's plunger is depressed, delivering the 100 units of botulinum toxin type A, thus providing linear, continuous subcutaneous distribution of the botulinum neurotoxin alongside the patient's left squamous suture 16. At a follow-up session 4 months post botulinum toxin administration, the patient reports that she has no headache pain since administered the neurotoxin and does not suffer from excessive tears and her nose is clear.

Example 5

A 32 year old construction worker reports to his doctor that ever since falling and injuring his C4-5 vertebrae on the job 2 years ago, he is beset with headaches that have been diagnosed as cervicogenic headaches. As a result, the patient suffers from a reduced range of neck motion and headache pain that is localized to the back, lower portion of his skull. The doctor determines to administer 100 units of a botulinum toxin type A (BOTOX®) in an inverted "V" configuration along and superimposed on at least a portion of the patient's lambdoid suture 10, starting at the apex of where the patient's sagittal suture 8 and lambdoid suture 10 lines meet at the back of his skull (as exemplified in FIG. 5) and proceeds downward and diagonally, following the lambdoid suture 10 line. 100 units of a botulinum toxin type A (BOTOX®) is reconstituted in a lotion vehicle. The doctor maps out the patient's lambdoid suture 10, parts the patient's hair accordingly and topically applies, using an swab applicator, the lotion vehicle carrying the botulinum toxin to the patients scalp along the length of the lambdoid suture 10 (in an inverted "V" shape).

The patient returns 3 months later and reports that he has only experienced one cervicogenic headache since topical application of the botulinum toxin along his suture lines. Additionally, the patient notes that his neck's range of motion has increased since the application of the botulinum toxin and that headache pain previously associated with turning his head too far to the left no longer manifests itself.

Botulinum neurotoxin may be administered by any suitable method as determined by the attending physician. The methods of administration disclosed herein permit the neurotoxin to be administered locally to a selected target suture line(s). Methods of administration include injection of a solution or composition containing the neurotoxin, as described above, and can also include implantation of a controlled release system along and within the vicinity of a targeted suture line, that controllably releases the neurotoxin. Such controlled release systems reduce the need for repeat injections. Diffusion of biological activity of a botulinum toxin within a tissue appears to be a function of dose and can be graduated. Jankovic J., et al Therapy With Botulinum Toxin, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of the headache pain and/or inflammation, and does not have negatively adverse effects on other neural systems. The botulinum toxin can be administered in accordance with the teachings provided herein by a transdermal route (e.g. by application of a Clostridial toxin in a cream, patch or lotion vehicle, as known in the art; see e.g. Published U.S. Patent Application No. 20040009180 A1, Ser. No. 10/194,805, filed Jul. 11, 2002, herein incorporated by reference) topically over the length or portion thereof of at least one suture line of the patient that is most proximal to a headache pain.

Additionally, while particular sutures have been referenced above, it is to be understood that the teachings of the instant invention can be utilized in reference to any suture line of the skull, as determined by an attending medical professional. For example, exemplary useful sutures that can be utilized in accordance with the teachings of the present disclosure include, but are not limited to, the sutura frontonasalis, sutura coronalis (a.k.a. coronal suture), sutura frontomaxillaris, sutura sphenofrontalis, sutura frontozygomatica, sutura squamosa (a.k.a. squamous suture), sutura frontolacrimalis, sutura sphenosquamosa, sutura lambdoidea (a.k.a. lambdoid suture), sutura parietomastoidea, sutura sphenozygomatica, sutura squamomastoidea, sutura occipitomastoidea, sutura lacrimomaxillaris, sutura temporozygomatica, sutura nasomaxillaris and sutura zygomaticomaxillaris, for example.

While injection via needle has been recited as one example of administration, local administration of a botulinum neurotoxin via an implant can provide a high, local therapeutic level of the toxin. A controlled release polymer capable of long term, local delivery of a Clostridial toxin to a target permits effective dosing at a desired suture line. A suitable implant, as set forth in U.S. Pat. No. 6,306,423 entitled "Neurotoxin Implant" allows the direct introduction of a chemotherapeutic agent to a target tissue, for example within the vicinity of a suture line, via a controlled release polymer. The implant polymers used are preferably hydrophobic so as to protect the polymer incorporated neurotoxin from water induced decomposition until the neurotoxin is released into the target tissue environment, here along at least one targeted suture line of the skull.

The method for treating headache according to the invention disclosed herein has many advantages, including the following:

1. avoids flooding of superficial structures that are associated with current injection techniques.

2. provides for patient-specific delivery of a medicament, such as a botulinum neurotoxin, to the bony surface of a patient's skull where nerve endings are accessible.

3. in general, a lower dose is required since the administration is focused.

4. reduces the potential of unwanted side effects, for example unwanted muscle weakness.

Various publications, patents and/or references have been cited herein, the contents of which are herein incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes administration methods to alleviate a headache pain wherein two or more neurotoxins, such as two or more botulinum toxins, are administered concurrently or consecutively to the vicinity and along with at least one suture line of a patient in need thereof. For example, botulinum toxin type A (e.g. BOTOX®) can be administered until a loss of clinical response or neutralizing antibodies develop, followed by administration of botulinum toxin type B (MYOBLOC®) in an amount of about 40-50 times the units of BOTOX® utilized.

Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect. A botulinum toxin can be administered by itself or in combination of one or more of the other botulinum toxin serotypes. The botulinum toxin can be a recombinantly made or a hybrid botulinum toxin.

My invention also includes within its scope the use of a neurotoxin, such as a botulinum toxin, in the preparation of a medicament for treating a patient suffering from a headache, comprising the step of administering a Clostridial toxin to a nerve located in the vicinity of at least one suture line of the patient's skull, wherein the administration alleviates at least one symptom of the headache. Additionally, it is to be understood that the whole of the length of the targeted suture line need not have a botulinum toxin administered thereto, that is, the amount/length of the suture line to which the botulinum toxin is administered is determined on a case by case basis by the attending medical practitioner.

Accordingly, the spirit and scope of the following claims should not be limited to the descriptions of the preferred embodiments set forth above.

I claim:

1. A method for treating a patient suffering from a headache, comprising the step of administering a Clostridial toxin between the periosteum and the aponeurotic fascia of the scalp in the vicinity of at least one suture line of the patient's skull, wherein the administration alleviates at least one symptom of the headache, thereby treating the patient suffering from the headache.

2. The method according to claim 1, wherein the Clostridial neurotoxin is a botulinum toxin.

3. The method according to claim 1, wherein the headache is selected from the group consisting of a sinus headache, a tension headache, a migraine headache, a cluster headache and a cervogenic headache.

4. The method according to claim 1, wherein the at least one suture line is selected from the group consisting of frontal suture, squamous suture, occipitomastoid suture, coronal suture, lambdoid suture and sagittal suture.

5. The method according to claim 2, wherein the botulinum toxin is selected from the group consisting of botulinum toxin types A, B, $C_1$, D, E, F and G.

6. The method according to claim 5, wherein the botulinum toxin is botulinum toxin type A.

7. The method according to claim 6, wherein amount of botulinum toxin type A administered is from about 5 units to about 1000 units.

8. The method according to claim 1, wherein the headache is an episodic migraine or a chronic migraine.

9. The method of claim 1, further comprising the step of administering the Clostridial toxin in the vicinity of a second suture line.

10. The method of claim 1, wherein the Clostridial neurotoxin is administered at about 1.5 cm, about 1.0 cm, or about 0.5 cm from the at least one suture line.

11. A method for alleviating a headache pain, comprising the step of determining the location of at least one suture line; and administering a therapeutically effective amount of botulinum toxin type A to a patient in need thereof, wherein the botulinum toxin type A is administered between the periosteum and the aponeurotic fascia of the scalp in the vicinity of the at least one suture line of the patient's skull, thereby alleviating the headache pain.

12. The method of claim 11, wherein the at least one suture line is selected from the group consisting of frontal suture, squamous suture, coronal suture, lambdoid suture, occipitomastoid suture and sagittal suture.

13. The method of claim 11, wherein the amount of administered botulinum toxin type A is from about 5 units to about 1000 units.

14. The method according to claim 12, wherein two or more of the frontal, squamous, coronal, lamboidal and sagittal sutures are administered botulinum toxin type A.

15. The method of claim 11, wherein the administration step includes the step of inserting a needle of a syringe containing the botulinum toxin type A at a needle penetration point, and positioning the needle along the at least one suture line so that the botulinum toxin type A is administered linearly along at least a portion of the at least one suture line.

16. The method of claim 11, further comprising the step of administering the botulinum toxin type A in the vicinity of a second suture line.

17. The method of claim 15, wherein one needle penetration point is utilized to administer the botulinum toxin type A in the vicinity of at least two suture lines.

18. The method of claim 11, wherein the botulinum toxin type A is administered at about 1.5 cm, about 1.0 cm, or about 0.5 cm from the at least one suture line.

19. The method of claim 1, wherein the administering is subdermal or subcutaneous.

20. The method of claim 11, wherein the administrating is subdermal or subcutaneous.

* * * * *